United States Patent
Pechko et al.

(10) Patent No.: US 7,744,911 B2
(45) Date of Patent: Jun. 29, 2010

(54) WATER BASED CLEAR SUNSCREEN AND INSECT REPELLENT COMPOSITION

(75) Inventors: Andrew H. Pechko, Ridgewood, NJ (US); Vincent T. Polywoda, Suffern, NY (US)

(73) Assignee: Avon Products, Inc, New York, NY (US)

( * ) Notice: Subject to any disclaimer, the term of this patent is extended or adjusted under 35 U.S.C. 154(b) by 644 days.

(21) Appl. No.: 11/510,304

(22) Filed: Aug. 25, 2006

(65) Prior Publication Data

US 2008/0050409 A1 Feb. 28, 2008

(51) Int. Cl.
*A01N 25/02* (2006.01)
*A01N 37/46* (2006.01)
(52) U.S. Cl. .................. 424/405; 424/59; 514/315; 514/351
(58) Field of Classification Search .................. None
See application file for complete search history.

(56) References Cited

U.S. PATENT DOCUMENTS

| 4,127,672 A | 11/1978 | Klier et al. |
|---|---|---|
| 5,000,937 A | 3/1991 | Grollier et al. |
| 5,145,604 A | 9/1992 | Neumiller |
| 5,716,602 A | 2/1998 | Uick |
| 5,916,541 A | 6/1999 | Stewart |
| 6,159,452 A | 12/2000 | Stewart |
| 6,517,816 B1 | 2/2003 | Gonzalez et al. |
| 6,719,959 B1 | 4/2004 | Gonzalez et al. |
| 2003/0129213 A1 | 7/2003 | Gonzalez et al. |
| 2003/0191154 A1 | 10/2003 | Kalafsky et al. |

*Primary Examiner*—Neil Levy
(74) *Attorney, Agent, or Firm*—Charles J Zeller; Joan M. McGillycuddy; Anthony M. Santini

(57) ABSTRACT

A clear, water based, homogeneous insect repellent sunscreen composition, comprising an oil soluble hydrophobic sunscreen component, an amido insect repellent component, an alcohol component, and water.

22 Claims, No Drawings

WATER BASED CLEAR SUNSCREEN AND INSECT REPELLENT COMPOSITION

BACKGROUND OF THE INVENTION

The present invention relates to a sunscreen and insect repellent composition, and more specifically to a clear, water-based sunscreen and insect repellent composition.

Outdoor daytime activities such as picnicking, hiking, fishing, swimming and exercise can expose people participating in these activities in certain environments to annoying and sometimes disease carrying insects, and to the damaging effects of ultraviolet (UV) exposure from both UVA and UVB radiation from the sun.

Insect repellents can provide a measure of relief from insects, which are not only a nuisance but can also be carriers of disease. Depending on the product, the insect repellent composition can be administered directly to the skin or clothing, or both, typically before anticipated exposure. The insect repellent can be in the form of a gel, lotion, cream, stick, mousse, wipe or spray and should be suitable for application to human skin in an amount sufficient to provide satisfactory insect repellency.

The concentration of insect repellent active contained in the composition will depend on the level of protection desired and can vary depending upon the specific insect repellent active used.

Sunscreen compositions can provide a measure of relief from exposure to the sun based on a scale of increasing protection from 1 to 50. The scale is called the Sun Protection Factor, or "SPF". The SPF value of a sunscreen allows consumers to determine the degree of sunburn protection they are willing to accept for a given period of time during direct exposure to the sun's ultraviolet rays. Additional information about SPF can be found in 21 CFR Part 352 *"Sunscreen Drug Products For Over-The-Counter Human Use"*.

Most commercially available insect repellents that contain sunscreen components are water-based opaque emulsions in the form of a cream or lotion.

There are other commercially available combination sunscreen and insect repellent formulations that are anhydrous. These anhydrous formulations are usually mixtures of different insect repellent actives and sunscreen oils that are generally in liquid form. These anhydrous formulations can also contain solid sunscreen compounds that solubilize in the oily sunscreen and/or insect repellent compounds.

DESCRIPTION OF THE PREFERRED EMBODIMENTS

The present invention comprises a clear, water based, homogeneous insect repellent sunscreen composition. The composition can be in the form of a water based gel, or a spray, such as an aerosol or a pump spray.

Homogeneity is an important characteristic of the insect repellent sunscreen composition because this type of composition is easier to spread onto the skin evenly. Homogeneity makes it easier to apply the composition by pump spray because the composition has a uniform viscosity. Additionally, no shaking is needed because there is only one stable phase.

The inventive insect repellent sunscreen composition can be prepared at ambient conditions and without emulsifiers. The subject invention can be produced for consumer use in the form of a gel or a spray package, either aerosol or pump.

The inventive insect repellent sunscreen composition is of sufficient clarity to enable text printed in 10-point type to be easily read through a 3-inch thickness of the liquid composition.

The amount of water in the insect repellent sunscreen composition can vary from about 2 weight % to about 40 weight %, preferably from about 5 weight % to about 35 weight %, and most preferably from about 10 weight % to about 30 weight % of the total weight of the composition.

The inventive insect repellent sunscreen composition contains one or more oil soluble liquid or solid sunscreen components in quantities sufficient to provide a Sun Protection Factor (SPF) above 2, and typically an SPF that varies from at least about 2 to about 55, and most commonly from about 8 to about 35. Most consumer sunscreen products are typically available with SPFs of 8, 15, 30, or 45.

The oil soluble sunscreen components of the inventive composition include, but are not limited to, benzophenone-3 (oxybenzone), dioxybenzone, menthyl anthranilate, para aminobenzoic acid (PABA), octyl methoxycinnamate (octinoxate), octocrylene, drometrizole trisiloxane, octyl salicylate (octisalate), homomenthyl salicylate (homosalate), octyl dimethyl PABA, butylmethoxy dibenzoylmethane (avobenzone), 4-methyl benzilidene camphor, octyl triazone, ethyl PABA, hydroxy methylphenyl benzotriazole, methylene bis-benzotriazoyl-tetramethylbutylphenol, bis-ethylhexyloxyphenol methoxyphenol triazine, and other equivalent oil-soluble sunscreens, and mixtures of the foregoing. These sunscreen components are hydrophobic and therefore, not miscible with water.

Other useful sunscreen actives include those disclosed in U.S. Pat. No. 5,000,937 to Grollier et al, which is incorporated by reference herein.

The amount of oil soluble sunscreen component can vary from about 1 weight % to about 45 weight %, preferably from about 5 weight % to about 40 weight %, and most preferably from about 10 weight % to about 35 weight % of the total weight of the insect repellent sunscreen composition.

The inventive insect repellent sunscreen composition also includes an amido insect repellent component. Suitable amido insect repellents include piperidine insect repellents such as picaridin {2-(2-hydroxy-ethyl)-1-piperidinecarboxylic acid 1-methylpropyl ester} (also known as icaridin, Bayrepel® or KBR3023, Lanxess Corp.) and its stereoisomers; 1-(3-cyclohexen-1-ylcarbonyl)-2 methylpiperidine (USDA compound code # AI3-37220) and its stereoisomers, or butylacetylaminopropionate ethyl ester (synonymously, beta-alanine, N-acetyl-N-butyl-, ethyl ester sold as IR3535®, Merck KGaA), and other equivalent insect repellents.

The amount of amido insect repellent component can vary from about 3 weight % to about 70 weight %, preferably from about 7 weight % to about 50 weight %, and most preferably from about 10 weight % to about 35 weight %, of the total weight of the insect repellent sunscreen composition.

The production of a clear, water based, homogenous composition containing oil soluble sunscreen components in combination with oil soluble insect repellent actives was unexpected because of the immiscibility of these hydrophobic compounds in water.

Accordingly, a water based insect repellent/sunscreen composition with an oil soluble sunscreen component and an oil soluble amido insect repellent component would be similarly expected to be formulated as an opaque emulsion aided by the use of emulsifiers and rheology agents.

However, it has been found, unexpectedly, that the amido insect repellent component serves as a co-solvent with a low molecular weight alcohol solvent, to enable the water and the oil soluble hydrophobic components to be combined to produce a clear, water based, homogeneous insect repellent sunscreen composition, without the need for emulsifiers.

It has also been found that as the concentration of the amido insect repellent component is increased, the insect repellent sunscreen composition can contain higher concentrations of water and lower concentrations of the alcohol solvent.

The low molecular weight alcohol component can vary from about 2 to 10 carbon atoms, preferably 2 to 4 carbon atoms, and can be linear, branched, or cyclic in its chemical structure.

Suitable alcohol compounds include ethanol, butanol, propyl alcohol, isopropyl alcohol, pentanol, methylcyclopentanol, hexanol, decanol, cyclohexanol, and the like.

The amount of alcohol component can vary from about 10 to about 60 weight %, preferably from about 15 weight % to about 40 weight %, and most preferably from about 25 weight % to about 35 weight % of the total weight of the insect repellent sunscreen composition.

The compositions of the present invention do not require the incorporation of emulsifiers because the compositions are single phase and homogeneous. Emulsifiers may also make the compositions more susceptible to removal during swimming or by perspiration, and can disrupt the skin's epidermal barrier lipids, thereby causing irritation. Accordingly, the compositions are preferably substantially emulsifier free, i.e., the compositions contain 1 weight % or less, preferably 0.5 weight % or less, and most preferably 0.1 to zero weight percent of an emulsifier.

Emulsifiers can be present, for example, when incorporated with a vendor supplied fragrance, or as a component of other vendor supplied adjuvants. Suitable emulsifiers are identified in the International Cosmetic Ingredient Dictionary and Handbook, $10^{th}$ Edition 2004, v. 3, Section 3, pages 2683-73 (INCI).

It has also been found that the optional addition of a polyol having about 3 to about 8 carbon atoms, preferably 3 to 6 carbon atoms, can improve the miscibility of the oil soluble sunscreen component and insect repellent component in the water based composition.

Suitable polyol components include butylene glycol, propylene glycol, dipropylene glycol, hexylene glycol, glycerin, sugar alcohols such as sorbitol, other equivalent polyols, and mixtures thereof.

The amount of polyol component in the insect repellent sunscreen composition can be up to about 20 weight %, typically from about 1 weight % to about 20 weight %, preferably from about 5 weight % to about 15 weight %, and most preferably from about 5 weight % to about 10 weight % of the total weight of the insect repellent sunscreen composition.

Other optional ingredients can also be included in the insect repellent sunscreen composition, such as film formers to extend the efficacy time of the insect repellent and to provide water/perspiration resistance or waterproofing properties to the insect repellent sunscreen composition.

The film former leaves a film residue on the surface of the skin either immediately or upon evaporation of the volatile components in the composition. The film former can also enhance the spread characteristics of the insect repellent sunscreen composition, which allows the composition to be more uniformly and consistently applied to the skin.

The film former can also help maintain the insect repellent at the surface of the skin for a longer period of time than it would otherwise remain without the film former. The film former can also provide sustained release of the insect repellent.

The amount of film former component in the insect repellent sunscreen composition will vary depending on desired film residue thickness and film properties. The film former in the present composition typically varies from about 0.05 weight % to about 10 weight %, and preferably from about 0.25 weight % to about 5 weight % based on the total weight of the insect repellent composition.

The film former component can be water-soluble, oil-soluble or both. Suitable film-formers include polymers, such as acrylates; copolymers such as acrylate/octylacrylamide copolymers and acrylate/vinyl acetate copolymers; cellulosic materials, such as methyl cellulose, hydroxyethyl cellulose hydroxypropyl cellulose; polyesters; polyurethane resins; and carbomers. Also suitable are synthetic clays, such as Laponite® available from Southern Clay Products, that are able to form transparent films and gels.

Additionally, the inventive composition may also contain a water soluble sunscreen, such as: sulisobenzone, TEA salicylate, terephthalylidene dicamphor sulfonic acid, phenylbenzimidazole sulfonic acid, other equivalent sunscreens, and mixtures thereof.

The insect repellent sunscreen composition does not require rheology agents such as thickening gums, clays or polymers to stabilize immiscible components. However, thickening agents can be used to prepare the composition in the form of a clear gel rather than a liquid. A suitable clay is the above-mentioned Laponite®. The preferred thickening polymer is carbomer.

In still another aspect of this invention, emollients, vitamins, fragrances, and colorants such as pigments or dyes including fluorescent dyes, glitters and pearlizing agents, can also be included in the insect repellent sunscreen composition to add distinctiveness to the formulation. These ingredients are well known in the art.

The compositions of the present invention are used by applying the compositions to the skin of humans in need of protection against sunlight and from insect bites. In the case of spray products, according to the invention, they are conveniently applied by expelling the contents of the container in which they are held through either an aerosol or pump spray nozzle. Thickened products such as gels are used by applying the product to the skin and spreading the product by hand.

The insect repellent sunscreen composition can be prepared under ambient conditions by mixing the components with conventional mixing equipment, such as a propeller-blade agitator. No emulsions or surfactants are necessary.

Typically, the at least one oil soluble hydrophobic sunscreen component, the at least one amido insect repellent component, the at least one low molecular weight alcohol component, and water are admixed, wherein the amido insect repellent component and the alcohol component function as co-solvents to solubilize the hydrophobic sunscreen component with the water component to produce the clear, homogenous insect repellent sunscreen composition.

Preferably, separate premixes of the water soluble and oil soluble ingredients are prepared, with the major portion and typically all of the alcohol and the polyol included in the premix of oil soluble ingredients.

A solid sunscreen component such as oxybenzone or avobenzone, if present in the formulation, is preferably the last ingredient to be incorporated into the oil ingredient premix. The water soluble ingredient and oil soluble ingredient premixes are then combined with mixing. Preferably, the aqueous premix is added to the oil ingredient premix with stirring.

In the examples that follow, all parts and percentages are by weight unless otherwise noted on an as is basis. All compositions were of sufficient clarity to enable the readability of text printed in 10-point type to be easily read through a 3 inch thickness of the inventive composition.

EXAMPLE 1

Spray Formulation (Estimated SPF 30 to 50)

| Component | % w/w |
|---|---|
| Alcohol SD 40B Anhydrous | 35.00% |
| Demineralized Water | 12.00% |
| Hexylene Glycol | 5.00% |
| Octyl Methoxycinnamate (Octinoxate) | 7.50% |
| Octyl Salicylate (Octisalate) | 5.00% |
| Benzophenone-3 (Oxybenzone) | 6.00% |
| Octocrylene | 8.00% |
| Film Former (Polyurethane-1) | 1.00% |
| Ethyl Butylacetylaminopropionate | 20.00% |
| Aloe | 0.10% |
| Vitamin E | 0.05% |
| Fragrance | 0.35% |
| | 100.00% |

EXAMPLE 2

Spray Formulation (Estimated SPF 15 to 25)

| Component | % w/w |
|---|---|
| Alcohol SD 40B Anhydrous | 45.20% |
| Demineralized Water | 20.00% |
| Hexylene Glycol | 15.00% |
| Octyl Methoxycinnamate (Octinoxate) | 5.00% |
| Oxybenzone (Oxybenzone) | 3.00% |
| Film Former (Polyurethane-1) | 1.00% |
| Ethyl Butylacetylaminopropionate | 10.00% |
| Aloe | 0.10% |
| Vitamin E | 0.50% |
| Fragrance | 0.20% |
| | 100.00% |

EXAMPLE 3

Spray Formulation (Estimated SPF 5 to 12)

| Component | % w/w |
|---|---|
| Alcohol SD 40B Anhydrous | 32.0000 |
| Demineralized Water | 28.9900 |
| Hexylene Glycol | 5.0000 |
| Octyl Methoxycinnamate (Octinoxate) | 5.0000 |
| Film Former (Polyurethane-1) | 1.0000 |
| Picaridin | 27.7500 |
| Aloe | 0.0100 |
| Vitamin E | 0.0500 |
| Fragrance | 0.2000 |
| | 100.00% |

EXAMPLE 4

Spray Formulation (Estimated SPF 10 to 20)

| Component | % w/w |
|---|---|
| Alcohol SD 40B Anhydrous | 25.7046 |
| Demineralized Water | 26.9454 |
| Hexylene Glycol | 7.5000 |
| Octyl Methoxycinnamate (Octinoxate) | 5.0000 |
| Octyl Salicylate (Octisalate) | 3.0000 |
| Film Former (Polyurethane-1) | 1.0000 |
| Picaridin | 30.5000 |
| Aloe | 0.1000 |
| Vitamin E | 0.0500 |
| Fragrance | 0.2000 |
| | 100.00% |

EXAMPLE 5

Spray Formulation (Estimated SPF 10 to 20)

| Component | % w/w |
|---|---|
| Alcohol SD 40B Anhydrous | 48.9500 |
| Demineralized Water | 15.0000 |
| Octinoxate (Parsol) | 7.5000 |
| Octyl Salicylate (Octisalate) | 5.0000 |
| Film Former (Polyurethane-1) | 3.3300 |
| Picaridin | 20.0000 |
| Aloe | 0.0100 |
| Vitamin E | 0.0100 |
| Fragrance | 0.2000 |
| | 100.00% |

The compositions 1 to 5 are applied directly onto the skin for UV protection and insect repellency.

What is claimed is:

1. A substantially emulsifier-free, clear, stable, single phase, water based, homogeneous insect repellent sunscreen composition, consisting essentially of:
   (a) about 1 weight % to about 45 weight % of a hydrophobic sunscreen component;
   (b) about 3 weight % to about 70 weight % of an amido insect repellent component;
   (c) about 10 weight % to about 60 weight % of at least one alcohol component having from 2 to 10 carbon atoms; and
   (d) 5 weight % to about 40 weight % of water, said components (b) and (c) being present in an amount sufficient to provide a clear homogeneous composition, and wherein the amido insect repellent component serves as a co-solvent with the low molecular weight alcohol component to enable the water component and the hydrophobic sunscreen component to be combined to produce the single phase, clear, stable, water based, homogeneous insect repellent sunscreen composition, said composition being substantially emulsifier-free, all percents being by weight of the total composition.

2. The composition of claim 1, wherein the oil soluble sunscreen component is at least one selected from the group consisting of benzophenone-3 (oxybenzone), dioxybenzone, menthyl anthranilate, para aminobenzoic acid (PABA), octyl methoxycinnamate (octinoxate), octocrylene, drometrizole trisiloxane, octyl salicylate (octisalate), homomenthyl salicylate (homosalate), octyl dimethyl PABA, butylmethoxy dibenzoylmethane (avobenzone), 4-methyl benzilidene camphor, octyl triazone, ethyl PABA, hydroxy methylphenyl benzotriazole, methylene bisbenzotriazoyl-tetramethylbutylphenol, bis-ethylhexyloxyphenol methoxyphenol triazine, and mixtures thereof.

3. The composition of claim 2, wherein the amido insect repellent component is at least one selected from the group consisting of piperidine insect repellents and butylacetylaminopropionate ethyl ester.

4. The composition of claim 3, wherein the piperidine insect repellent is at least one selected from the group consisting of picaridin and its stereoisomers, 1-(3-cyclohexen-1-ylcarbony 1)-2-methylpiperidine and its stereoisomers, and mixtures thereof.

5. The composition of claim 1, also including at least one water soluble sunscreen component selected from the group consisting of sulisobenzone, triethanolamine salicylate, terephthalylidene dicamphor sulfonic acid, phenylbenzimidazole sulfonic acid, and mixtures thereof.

6. The composition of claim 1, wherein the amido insect repellent component varies from about 7% to about 50% by weight of the total composition.

7. The composition of claim 1, wherein the alcohol component is at least one selected from the group consisting of ethanol, butanol, propyl alcohol, isopropyl alcohol, pentanol, methylcyclopentanol, hexanol, decanol, cyclohexanol, and mixtures thereof.

8. The composition of claim 1, also including at least one film former.

9. The composition of claim 8, wherein the film former is selected from the group consisting of acrylate polymers, acrylate copolymers, polyesters, cellulosic materials, polyurethane resins, carbomers, and mixtures thereof.

10. The composition of claim 1, wherein sunscreen component is a liquid.

11. The composition of claim 1, wherein the sunscreen component is a solid.

12. The composition of claim 1, wherein the sunscreen composition has a Sun Protection Factor that varies from about 2 to about 60.

13. The composition of claim 1, also including a polyol component.

14. The composition of claim 13, wherein the polyol component is at least one selected from the group consisting of butylene glycol, dipropylene glycol, propylene glycol, hexylene glycol, glycerin, and mixtures thereof.

15. The composition of claim 14, wherein the polyol component varies from about 1% to about 20% by weight of the total composition.

16. The composition of claim 1, wherein the sunscreen is present in an amount of from about 5% to about 35%; the amido insect repellent is present in an amount of from about 10% to about 35%; the at least one alcohol is present in an amount of from about 15% to about 60%, and water is present in an amount of from about 10% to about 35%, the composition having an Sun Protection Factor of from about 8 to about 45.

17. The composition of claim 16, also including a polyol component present in an amount of from about 1 weight % to about 20 weight % and a film former present in an amount of from about 0.05 weight % to about 10 weight %.

18. The composition of claim 17, wherein the sunscreen is selected from the group consisting of benzophenone-3 (oxybenzone), dioxybenzone, menthyl anthranilate, para aminobenzoic acid (PABA), octyl methoxycinnamate (octinoxate), octocrylene, drometrizole trisiloxane, octyl salicylate (octisalate), homomenthyl salicylate (homosalate), octyl dimethyl PABA, butylmethoxy dibenzoylmethane (avobenzone), 4-methyl benzilidene camphor, octyl triazone, ethyl PABA, hydroxy methylphenyl benzotriazole, methylene bisbenzotriazoyl-tetramethylbutylphenol, bis-ethylhexyloxyphenol methoxyphenol triazine, and mixtures thereof; wherein the amido insect repellent is at least one selected from the group consisting of piperidine insect repellents and butylacetylaminopropionate ethyl ester; wherein the alcohol is selected from the group consisting of ethanol, butanol, propyl alcohol, isopropyl alcohol, pentanol, methylcyclopentanol, hexanol, decanol, cyclohexanol, and mixtures thereof; and wherein the polyol component is selected from the group consisting of butylene glycol, dipropylene glycol, propylene glycol, hexylene glycol, glycerin, and mixtures thereof.

19. The composition of claim 18, wherein the film former is selected from the group consisting of acrylate polymers, acrylate copolymers, polyesters, cellulosic materials, polyurethane resins, carbomers, and mixtures thereof, and is present in an amount of from about 0.25 weight % to about 5 weight %.

20. A method for preparing a clear, water based, homogeneous insect repellent sunscreen composition of claim 1 comprising:
(a) admixing at least one oil soluble hydrophobic sunscreen component, at least one amido insect repellent component, at least one low molecular weight alcohol component, and water; wherein the amido insect repellent component and the alcohol component function as co-solvents to solubilize the hydrophobic sunscreen component with the water component to produce the clear, homogenous insect repellent sunscreen composition 21. The method of claim 20, also including admixing the components with at least one polyol.

22. The method of claim 20, wherein a first premix is formed comprising the sunscreen component, the amido insect repellent component, and the one low molecular weight alcohol component, wherein a second premix is formed comprising water, and wherein the second premix is added to the first premix with agitation.

* * * * *